United States Patent [19]
Zlotnik

[11] Patent Number: 5,376,338
[45] Date of Patent: Dec. 27, 1994

[54] AIR TREATING APPARATUS AND CARTRIDGE FOR SUCH APPARATUS

[75] Inventor: Arnold H. Zlotnik, Monroeville, Pa.

[73] Assignee: Pestco, Inc., Braddock, Pa.

[21] Appl. No.: 62,345

[22] Filed: May 17, 1993

[51] Int. Cl.⁵ .............................................. A61L 9/00
[52] U.S. Cl. ...................................... 422/124; 422/5; 422/122; 422/123; 239/60
[58] Field of Search ............... 422/4, 5, 122, 123, 422/124; 239/60

[56] References Cited

U.S. PATENT DOCUMENTS

| | | | |
|---|---|---|---|
| 4,035,451 | 7/1977 | Tringali | 422/4 |
| 4,059,422 | 11/1977 | Steiner | 422/124 |
| 4,707,338 | 11/1987 | Spector | 422/5 |
| 4,743,406 | 5/1988 | Steiner et al. | 422/124 |
| 4,931,224 | 6/1990 | Holzner, Sr. | 422/124 |
| 5,230,867 | 7/1993 | Kunze et al. | 422/5 |

Primary Examiner—Timothy M. McMahon
Attorney, Agent, or Firm—Hymen Diamond

[57] ABSTRACT

A replacable cartridge for air-treating apparatus which includes a blower for generating an air stream. The cartridge includes a battery on which a seat in the form of a cap or sleeve having a flange is mounted and with a porous block to be impregnated with a vaporizable air-treating material seated on the flange. The block has peripheral holes in whose surfaces the vaporizable material is absorbed and from which the vapor is released. The holes are unobstructed by the seat. The battery is connected to energize the blower which produces a stream of air to pass over the surfaces of the holes and produce the vapor.

19 Claims, 3 Drawing Sheets

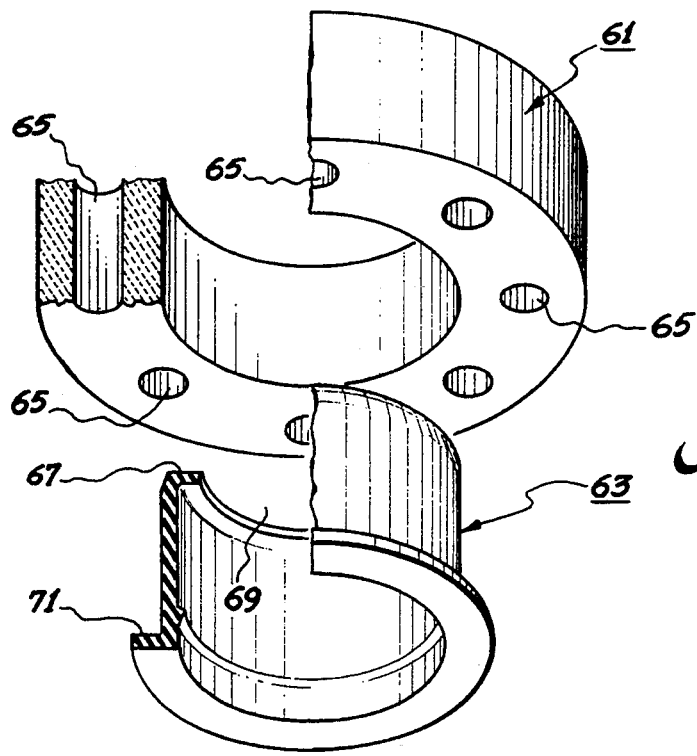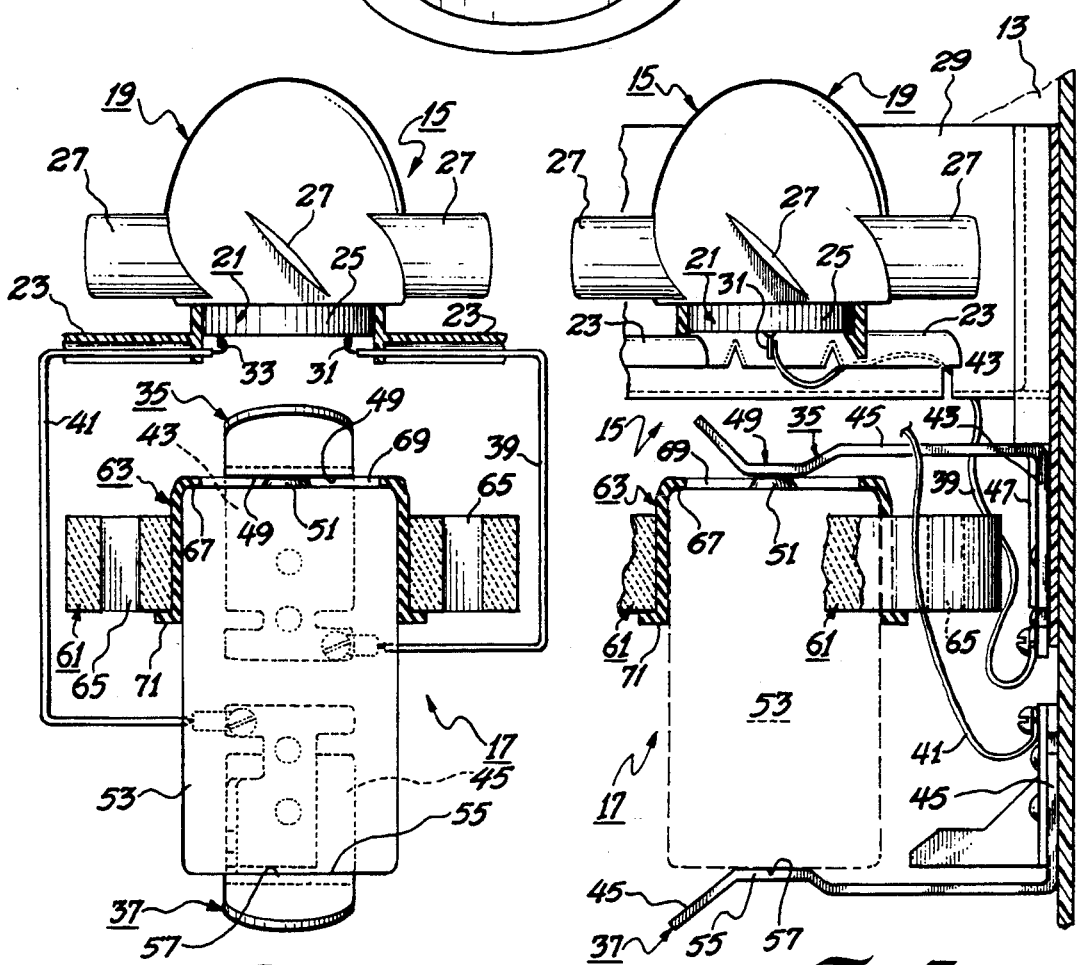

AIR TREATING APPARATUS AND CARTRIDGE FOR SUCH APPARATUS

REFERENCE TO RELATED APPLICATION

This application relates to application Ser. No. 07/827,081, filed Jan. 23, 1992 to Clifford B. Zlotnik and Arnold H. Zlotnik, for CARTRIDGE FOR DEODORIZING, DISINFECTING OR HUMIDIFYING APPARATUS (herein Zlotnik), and incorporated in this application by reference.

BACKGROUND OF THE INVENTION

This invention relates to the art of diffusing into the air of a region the vapor from a vaporizable material for deodorizing, disinfecting or humidifying or in other ways treating the air in the region. The treatment whether it be deodorizing, disinfecting or humidifying the region or treating the air in any other way is in this application referred to as "air treatment." This invention has particular relationship to apparatus for air treatment which includes a motor-driven blower for producing a stream of air which releases vapor of air-treating, vaporizable material from a porous solid impregnated with the material and which is provided with a replacable cartridge including a power supply for energizing the motor and the porous solid. This invention also has particular relationship to the replacable cartridge for such apparatus.

Zlotnik discloses apparatus and a cartridge as generally described above. FIG. 1 of Zlotnik discloses apparatus 11 including an air-stream generating assembly 15 having motor 25 and blower 27 and the cartridge 17, which includes the battery 43 and the annular porous block 53 that is impregnated with the vaporizable material from which vapor is released by the air stream. Zlotnik's apparatus has performed satisfactorily, but it is desirable that the cartridge be further simplified to further facilitate the handling of the cartridge in storage, shipment and replacement and to achieve substantial cost reduction.

It is an object of this invention to accomplish this purpose and to provide a cartridge of simpler and less complicated structure and less costly than the Zlotnik cartridge and which lends itself readily to simplified handling and is less costly.

SUMMARY OF THE INVENTION

It has been realized in arriving at this invention that the container 55 of Zlotnik's cartridge is a major contributor to the problems encountered in the manufacture, storage and handling during replacement and to its cost. The container is typically composed of heavy duty polyethylene or polypropylene and is molded. The dies, the material and the molding operation constitute a substantial factor in the cost of the cartridge. In addition, the handling demanded by the cartridge and its container during replacement materially complicates this task.

In accordance with this invention there is provided a cartridge without a container such as 55 of Zlotnik, thus eliminating all of the complications and costs which the container entails. In the practice of this invention, there is provided a replacable cartridge including a battery and a porous block adapted to be impregnated with vaporizable material. The porous block, typically of annular shape, is mounted on a seat on the battery. The seat is a flange on a sleeve which is mounted on the battery. The sleeve may be a cylindrical cap having a base at one end with a flange extending from its cylindrical wall. The cap is mounted on the upper end of the battery. Its base has an opening affording access for connection to the upper pole of the battery. The flanged cap may also be mounted on the lower end of the battery or a flanged sleeve may be mounted between the ends of the battery or in some cases, an annular disc or ring may be mounted. In this cases the cap or sleeve or disc must be a tight fit on the battery. In all cases, except that involving the disc, the wall of the cap or sleeve is interposed between the annular block and the battery and prevents the penetration of the vapor of the material with which the block is impregnated into the battery. The cap on the lower end and disc can only be used where the penetration of vapor into the battery is not a significant factor.

The air stream produced by the blower passes through the block to vaporize the material with which the block is impregnated. For this purpose, the block is provided with holes around its periphery. The block is so mounted on the supporting means, i.e., the supporting annulus extending from the battery, that the holes are substantially unobstructed. To achieve this purpose, the radial dimension of the supporting means must be such that the holes or a substantial area of the holes extend beyond the supporting member. Alternatively, the supporting means may extend under the area of the annulus containing the holes, but may be provided with holes coextensive with the holes in the block.

BRIEF DESCRIPTION OF THE DRAWINGS

For a better understanding of this invention, both as to its organization and to its method of operation, together with additional objects and advantages thereof, reference is made to the following description taken in connection with the accompanying drawings, in which:

FIG. 2 is a fragmental view in side elevation and partly in section showing from one aspect the essential feature of the apparatus shown in FIG. 1;

FIG. 3 is a fragmental view in side elevation and partly in section similar to FIG. 2 as seen from another aspect;

FIG. 4 is an exploded view in isometric showing the relationship of the annular block and the cap of the apparatus shown in FIG. 1.

DETAILED DESCRIPTION OF EMBODIMENT

Figure 1:
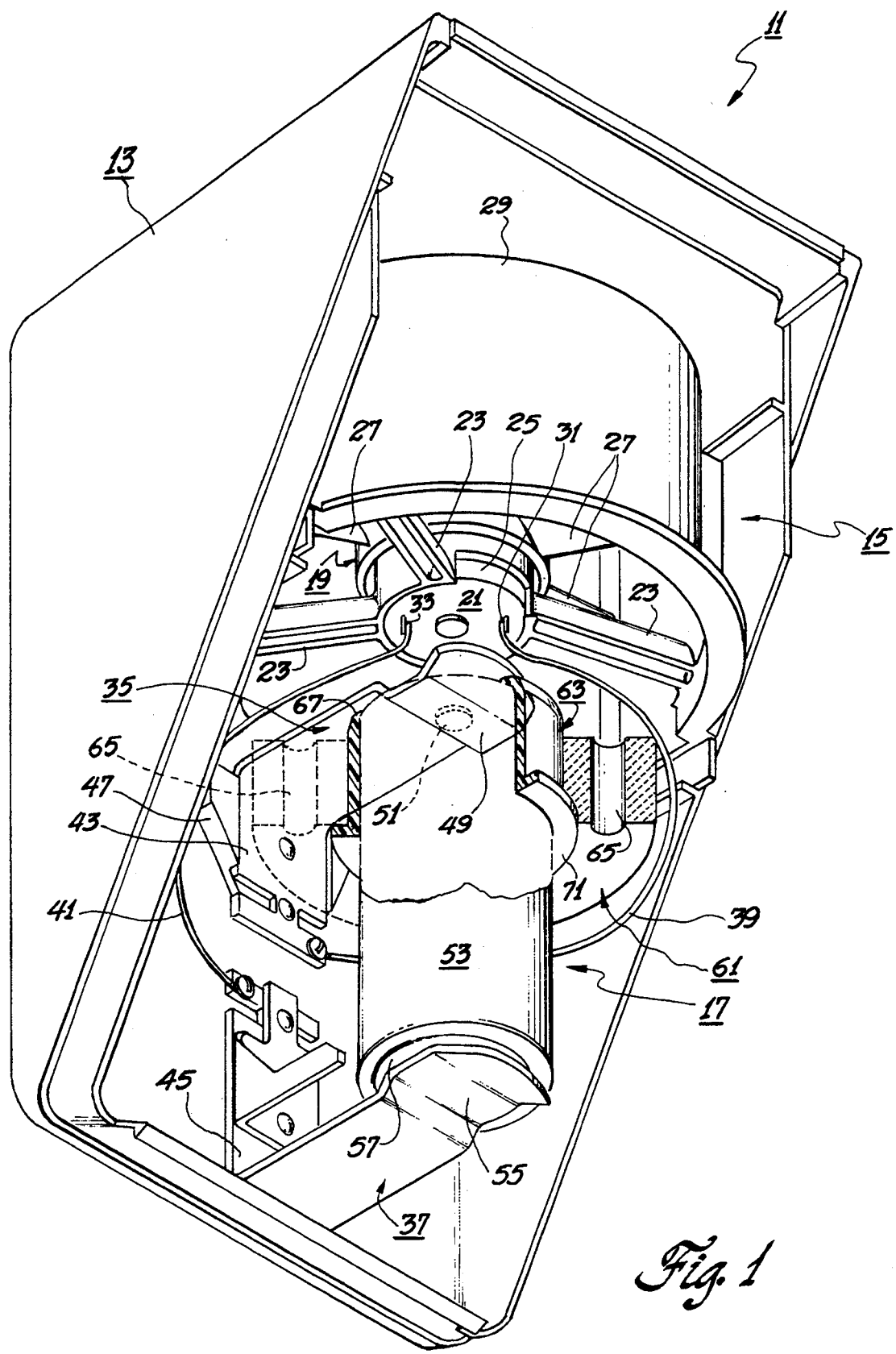
FIG. 1 is a view in isometric of air-treating apparatus in accordance with this invention, with the front cover of the casing removed, and including a cartridge in accordance with this invention constituting an embodiment of this invention.

The air-treating apparatus 11 shown in FIGS. 1 through 4 includes the mounting section 13 of a housing which is typically mounted on the wall of a region being treated. A closure section (not shown) is secured to the mounting section 13 to form the complete housing. Within the section 13, there is an air-stream generating assembly 15 and a cartridge 17 for energizing the assembly 15 and providing the vapor which is diffused into the air of the region.

The air-stream generating assembly includes a blower or fan 19 and a motor 21 connected to drive the blower 19. The blower 19 and the motor are supported as a rigid unit from the wall of the section 13 by radial spiders 23, each secured at the inner end to the motor case 25 and at the other end of the wall of section 13. The blades 27 of the blower 19 extend into an air-treatment tube 29 through which the vapor-containing air is driven by the blower 19. The tube 29 is suspended from the wall of section 13. The motor terminals 31 and 33 are connected to battery terminals 35 and 37 by conductors 39 and 41. The battery terminals 35 and 37 are typically composed of spring steel or other like alloy. Each terminal is of annular shape, the angle between its arms 43 and 45 being somewhat less than 90°. The arm 43 of terminal 35 is secured to the bracket 47 from which the air-treatment tube 29 is suspended from the wall of section 13. The arm 45 of the battery terminal 37 is secured directly to the wall of section 13. The terminal 35 has a flat projection 49 contacting the pole 51 of the battery 53 of the cartridge 17. The terminal 37 has a flat projection 55 for contacting pole 57 of the battery 53.

The cartridge 17 includes, in addition to the battery 53, an annular porous block 61 and a sleeve or cap 63 which extends over one end of the battery 53. As disclosed in Zlotnik, the block 61 may be typically composed of a mixture of a binder with plaster of Paris and terra cotta material. The components are moistened and mixed in a powder ribbon blender to a paste. The paste is then formed in a die and heated in a kiln to hardness. The block may also be composed of other material such as porous wood, cloth or paper or other plastic and fiber materials. The block 61 has holes 65 through which the air stream from blower 19 passes and whose surfaces enchance the area available for absorption of the vaporizable material and release of the vapor.

The cap 63 has a base 67 with a hole 69 (FIGS. 2, 3, 4) in it and a flange 71. The block 61 is seated on the flange 71. As shown in FIGS. 1 through 3 the radial width of the flange 71 is such that the holes 65 in the block 61 are entirely unobstructed. The holes 65 may be partially obstructed by the flange 71, but there should be a substantial area of the holes unobstructed to assure effective release of the vaporizable material by the air stream.

In use, of the apparatus shown in FIGS. 1, 2, 3, the air-stream generating assembly is mounted in section 13 of the apparatus 11. The replacable cartridge 17 is assembled and is mounted between the terminals 35 and 37, with the projections 49 and 55 of the terminal tightly engaged with battery 53 at poles 51 and 57. The replacable cartridge is held firmly between the terminals 35 and 37. The blower motor 21 is energized producing a stream of air which envelopes the block 61 and passes through the holes 65, releasing the vapor of the vaporizable material into the air of the region to be treated. With the block 61 properly impregnated, replacement of the cartridge 17 or the block or the battery is demanded only about once a month.

Figure 5:
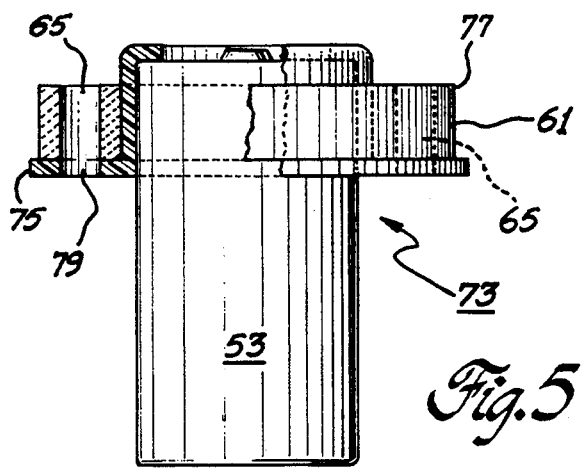
FIGS. 5, 6, 7, 8 each is a view in side elevation showing different modifications of this invention.

An alternative assembly 73 is shown in FIG. 5. In this case the flange 75 of the cup 77 extends under the part of the block 61 which has the holes 65. To preclude obstruction of the holes, the flange 75 is provided with holes 79 which are coextensive with holes 65 in the block 61.

Figure 6:
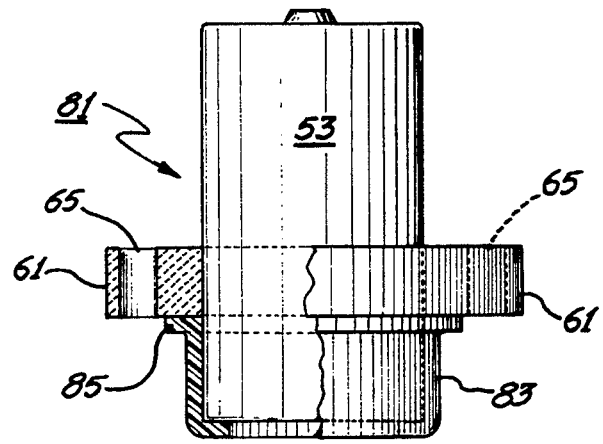

The cartridge 81, shown in FIG. 6, includes a cap 83 which is mounted on the lower end of the battery 53. The flange 85 extends from the upper end of the cap. The block 61 is seated on the flange 81. The cap 83 engages the lower end of the battery tightly.

Figure 7:
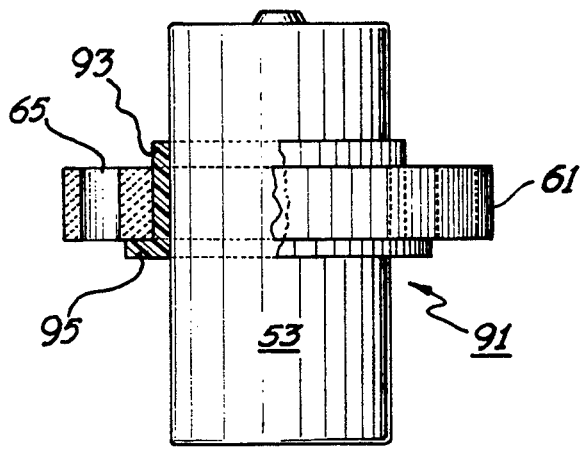

The cartridge 91 of FIG. 7 includes a sleeve 93 having a flange 95 mounted on the battery 53 intermediate its ends. The block 61 is mounted on the flange 95. The radial width of the flange is such that holes 65 in the block 61 are not obstructed. The sleeve 93 engages the battery 53 tightly.

Figure 8:
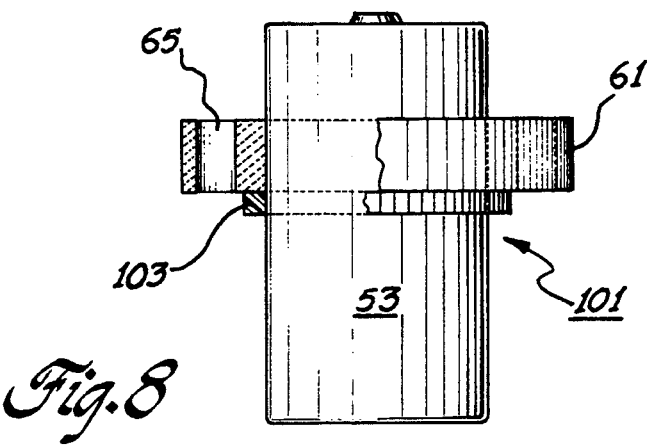

The cartridge 101 of FIG. 8 includes an annular or flat ring 103 which engages the battery 53 tightly. The block 61 is seated on the annulus 103.

While preferred embodiments of this invention have been disclosed herein, many modifications thereof are feasible. This invention is not to be restricted except insofar as is necessitated by the spirit of the prior art.

I claim:

1. A replacable cartridge for use in air-treating apparatus having blower means, when energized, for producing a stream of air and a replacable cartridge, connected to said blower means, adapted to connect said blower means to a power supply means for energizing said blower means; said replacable cartridge including, sans a container surrounding said cartridge: a battery, vaporizable air-treating means including a porous block adapted to be impregnated with a vaporizable material to be vaporized for treating air, and means mounted on said battery, for supporting said block on said battery, there being no container surrounding said porous block and said battery and supporting said block on said battery, said apparatus being adapted to receive said cartridge with said battery connected to said connecting means in energizing relationship with said blower means and said annular porous block in the path of the resulting stream of air, whereby said vaporizable material in said block is vaporized.

2. Air-treating apparatus having blower means, when energized, for producing a stream of air, and a cartridge including, sans a container surrounding said cartridge, a battery for energizing said blower means, vaporizable air-treating means including a porous block adapted to be impregnated with vaporizable material to be vaporized for treating air, means, connected to said blower means, for connecting said battery in energizing relationship with said blower means to produce a stream of air, and means, mounted on said battery for supporting said block on said battery in said stream of air to vaporized said material, there being no container surrounding said battery and said porous block and supporting said porous block on said battery.

3. The replacable cartridge of claim 1 wherein the battery is generally cylindrical and has a pole accessible through the surface of one end thereof and the block-supporting means is a generally cylindrical cap having a base with an opening therein at one end thereof and a flange extending from the cylindrical surface of said cap, said cap being mounted on said one end of said battery with said pole accessible through said opening, the block being seated on said flange, and the energizing means being adapted to be electrically connected to said pole.

4. The air-treating apparatus of claim 2 wherein the battery is generally cylindrical and has a pole accessible through the surface on one end thereof and the block-supporting means is a generally cylindrical cap having a base having an opening therein at one end thereof and a flange extending radially therefrom, said cap being mounted on said one end of said battery with said pole accessible through said opening, said block being seated on said flange, and the connecting means being connected to said pole.

5. The replacable cartridge of claim 1 wherein the block is of annular shape having a central opening therein, said block being supported on the supporting means with said central opening encircling said battery.

6. The apparatus of claim 2 wherein the block is of annular shape having a central opening and said block being supported on the supporting means with said central opening encircling said battery.

7. A replacable cartridge for use in air-treating apparatus having blower means for producing a stream of air and terminals for connection to a power supply for energizing said blower means; said replacable cartridge including, sans a container surrounding said cartridge: a battery, an annular porous block having an opening therein, said block being adapted to be impregnated with vaporizable air-treating material, and a cylindrical cap for said battery having a base and seating means for said block, said cap being seated on one end of said battery with said seating means extending radially from said battery, said block being seated on said seating means with said opening encircling said battery, there being no container surrounding said battery and said porous block and supporting said porous block on said battery, said cartridge being adapted to be mounted in said apparatus with said battery in energizing relationship with said blower means through said terminals and said block positioned in the path of said stream of air, whereby said stream of air vaporizes said material releasing said vapor for air treating.

8. A replacable cartridge for use in air-treating apparatus, said apparatus having blower means for producing a stream of air and terminals for connection to a power supply for energizing said blower means, said blower means having means adapted to mount and be energized by said replacable cartridge; said replacable cartridge including, sans a container surrounding said cartridge: an annular porous block adapted to be impregnated with a vaporizable air-treating material, said block having a generally central opening therein, a battery having a pole adapted to be accessed by a said terminal at the surface of one end thereof, and a cap having a cylindrical wall and a base with an opening therein at one end and having a flange extending from said cylindrical wall, said cap being mounted on said one end of said battery with said base extending over the surface of said one end with said cylindrical wall encircling said battery and with said opening in said base adapted to afford access for connection of a said terminal of said apparatus to the pole of said battery at said one end, said block being mounted on said flange with its said generally central opening enveloping the cylindrical wall of said cap contiguous to said flange, there being no container surrounding said porous block and said battery and supporting said porous block on said battery.

9. The replacable cartridge of claim 1 wherein the block is of annular shape and has a plurality of holes between its inner boundary and its outer boundary providing surfaces for impregnation of the block with vaporizable material and release of the vapor of the material by the air stream, and the block supporting means is structured to support the block with said holes substantially unobstructed.

10. The apparatus of claim 2 wherein the block is of annular shape and has a plurality of holes between its inner boundary and its outer boundary providing surfaces for impregnation of the block with vaporizable material and release of the vapor of the material by the air stream and the block supporting means is structured to mount the block with said holes substantially unobstructed.

11. The replacable cartridge of claim 9 wherein the block supporting means is structured to extend under the portion of the block having the peripheral holes and includes holes coextensive with said peripheral holes whereby the holes in the block are substantially unobstructed.

12. The apparatus of claim 10 wherein the block supporting means is structured to extend under the portion of the block having the peripheral holes and includes holes coextensive with said peripheral holes whereby the holes in the block are substantially unobstructed.

13. A replacable cartridge for air-treating apparatus including, sans a container surrounding said cartridge, a generally cylindrical battery, vaporizable air-treating means including a member adapted to be vaporized to release vapor into air to be treated and means, mounted on said battery, for supporting said member accessible to a vapor releasing air stream, there being no container surrounding said battery and said member and supporting said member on said battery.

14. The cartridge of claim 13 wherein the member is annular having a generally central opening therethrough and the supporting means is means, mounted on said battery, having a surface extending radially from said battery on which the member is supported with its generally central opening encircling said battery.

15. Air-treating apparatus including blower means, a motor when energized for driving said blower means to produce a stream of air; a cartridge including, sans a container surrounding said cartridge, a battery, vaporizable air-treating means including an annular member supported generally coaxially on said battery, there being no container surrounding said battery and said member and supporting said member on said battery, said member being adapted to contain vaporizable air-treating material which when said member is subjected to a stream of air, releases said material as vapor into air to be treated, battery terminals mounting said cartridge by engagement with the poles of said battery, and means, connecting said battery terminals to said motor, to energize said motor driving and blower means to produce a stream of air, said cartridge being mounted by the battery terminals with said member in the stream of air.

16. The apparatus of claim 15 wherein the poles are at the ends of the battery and the battery terminals support the cartridge by engaging the battery at the ends thereof.

17. The apparatus of claim 15 wherein the battery terminals are composed of spring steel or like alloy holding the cartridge firmly by tight engagement with the terminals.

18. The replacable cartridge of claim 13 wherein the member is a porous block adapted to be impregnated with vaporizable air-treating material which, when said block is subjected to the air stream, is adapted to be vaporized to release vapor into the air to be treated.

19. The apparatus of claim 15 wherein the member is a block of porous material supported generally coaxially on said battery, said block being adapted to be impregnated with vaporizable air-treating material which, when said block is subjected to the air stream, releases said material as vapor in the air to be treated.

* * * * *